United States Patent
Aoki et al.

(10) Patent No.: US 6,333,420 B1
(45) Date of Patent: Dec. 25, 2001

(54) PROCESS FOR PRODUCING EPICHLOROHYDRIN AND INTERMEDIATE THEREOF

(75) Inventors: Takanori Aoki; Takami Ohe; Haruki Ishikami, all of Kawasaki (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 09/589,078

(22) Filed: Jun. 8, 2000

Related U.S. Application Data

(60) Provisional application No. 60/140,824, filed on Jun. 28, 1999, and provisional application No. 60/140,842, filed on Jun. 28, 1999.

(30) Foreign Application Priority Data

| Jun. 8, 1999 | (JP) | ................................................. 11-161383 |
| Jun. 8, 1999 | (JP) | ................................................. 11-161384 |
| Apr. 28, 2000 | (JP) | ................................................. 12-131145 |
| Apr. 28, 2000 | (JP) | ................................................. 12-131146 |

(51) Int. Cl.[7] ......................... C07D 301/27; C07C 29/00
(52) U.S. Cl. ........................................... 549/514; 568/850
(58) Field of Search ............................ 568/850; 549/514

(56) References Cited

U.S. PATENT DOCUMENTS

| 1,841,279 | 1/1932 | Dow . | |
| 2,043,932 | 6/1936 | Ferdinand et al. . | |
| 2,099,231 | 11/1937 | Ruys et al. . | |
| 2,441,287 | 5/1948 | Ramage . | |
| 4,479,020 | * 10/1984 | Suciu et al. | .......................... 568/850 |
| 5,227,541 | * 7/1993 | Mori et al. | ........................... 568/850 |
| 6,051,742 | * 4/2000 | Green et al. | .......................... 568/850 |

FOREIGN PATENT DOCUMENTS

| 59-51933 | 12/1984 | (JP) . |
| 60-258172 | 12/1985 | (JP) . |
| A-60-258171 | 12/1985 | (JP) . |
| A-62-26243 | 2/1987 | (JP) . |
| 62-41488 | 9/1987 | (JP) . |
| 62-51246 | 10/1987 | (JP) . |
| 1-22250 | 4/1989 | (JP) . |
| 1-34206 | 7/1989 | (JP) . |
| 2-40049 | 9/1990 | (JP) . |
| 2-47967 | 10/1990 | (JP) . |
| 5-7377 | 1/1993 | (JP) . |
| 6-25196 | 4/1994 | (JP) . |
| 11-343265 | 12/1999 | (JP) . |

OTHER PUBLICATIONS

Matsuoka et al, CA110:76261, 1989.*

* cited by examiner

*Primary Examiner*—Deborah C. Lambkin
(74) *Attorney, Agent, or Firm*—Sughrue, Mion, Zinn, Macpeak & Seas, PLLC

(57) ABSTRACT

Allyl alcohol and chlorine are reacted in a gaseous phase to efficiently produce dichloropropanol and, using the dichloropropanol so produced, epichlorohydrin is efficiently produced.

22 Claims, No Drawings

PROCESS FOR PRODUCING EPICHLOROHYDRIN AND INTERMEDIATE THEREOF

CROSS-REFERENCE TO RELATED APPLICATIONS

This application is an application filed under 35 U.S.C. §111(a) claiming benefit pursuant to 35 U.S.C. §119(e)(1) of the filing date of the Provisional Applications 60/140,824 and 60/140,842 filed Jun. 28, 1999, pursuant to 35 U.S.C. §111(b).

BACKGROUND OF THE INVENTION

1. Field of the Invention

The present invention relates to a process for the production of epichlorohydrin and dichloropropanol which is an intermediate of epichlorohydrin. Epichlorohydrin is useful as a raw material for the production of various compounds or as a solvent, a raw material for epoxy resins, a raw material for synthetic rubbers, a stabilizer for chlorinated rubbers and the like.

2. Description of the Related Art

Epichlorohydrin is produced through a step of reacting allyl alcohol with chlorine to produce dichloropropanol and a step for dehydrochlorinating dichloropropanol to produce epichlorohydrin.

The term "dichloropropanol" as used herein refers to 2,3-dichloro-1-propanol, 1,3-dichloro-2-propanol or a mixture thereof.

A process for producing dichloropropanol by reacting allyl alcohol with chlorine is known and described in Japanese Unexamined Patent Publication (Kokai) Nos. 60-258171 and 62-26243.

In all of these conventional techniques, the reaction is effected in a liquid phase, and allyl alcohol and chlorine are reacted in the presence of hydrochloric acid or hydrogen chloride. However, the use of hydrochloric acid or hydrogen chloride is industrially disadvantageous since a recovery step therefor is necessary or loss of hydrochloric acid or hydrogen chloride is caused at the time of recovery. Furthermore, since the reaction of allyl alcohol with chlorine to produce dichloropropanol is an exothermic reaction, external cooling or the like is necessary in order to obtain dichloropropanol with high efficiency and this causes a loss of energy and the like.

As a conventional technique for chlorination in a gaseous phase, a reaction of ethylene with chlorine is known (see, for example, U.S. Pat. No. 2,099,231). However, a method of producing dichloropropanol by reacting allyl alcohol with chlorine in a gaseous phase has not hitherto been reported.

BRIEF SUMMARY OF THE INVENTION

An object of the present invention is to solve the problems in conventional production methods for dichloro-propanol, i.e., in the liquid phase chlorination methods, in a process for producing epichlorohydrin. More specifically, it is to solve problems attributable to the use of hydrochloric acid or hydrogen chloride, such as need of a step for recovering hydrochloric acid or hydrogen chloride, recovery loss thereof, and energy loss accompanying the external cooling, so that dichloropropanol can be produced industrially advantageously, whereby a process for producing epichlorohydrin more industrially advantageous can be provided.

As a result of extensive investigations to solve the above-described problems, the present inventors have found that the object of the present invention can be attained by a process, for producing dichloropropanol, comprising reacting allyl alcohol with chlorine in a gaseous phase. The present invention has been accomplished based on this finding.

In other words, the present invention provides a process for producing dichloropropanol comprising reacting allyl alcohol with chlorine in a gaseous phase.

Further, the present invention provides a process for producing epichlorohydrin comprising:

a first step of reacting allyl alcohol with chlorine in a gaseous phase to produce dichloropropanol; and a second step of dehydrochlorinating dichloropropanol obtained at the first step to produce epichlorohydrin.

DETAILED DESCRIPTION OF THE INVENTION

The present invention will be described in detail below.

The allyl alcohol for use in the present invention may be any commercially or industrially available allyl alcohol and is not particularly limited.

The chlorine for use in the present invention may be any commercially or industrially available chlorine and is not particularly limited.

The reaction of allyl alcohol with chlorine in a gaseous phase may preferably be effected in the presence of a catalyst.

The catalyst for use in the production of dichloropropanol according to the present invention may suitably be a catalyst containing at least one element selected from the elements of Groups 1 to 16 of the long-form Periodic Table or at least one compound containing the at least one element. Examples of the element include Li, Na, K, Rb and Cs of Group 1 of the long-form Periodic Table, Be, Mg, Ca, Sr and Ba of Group 2, Y, Sc, lanthanoid element and actinoid element of Group 3, Ti, Zr and Hf of Group 4, V, Nb and Ta of Group 5, Cr, Mo and W of Group 6, Mn, Tc and Re of Group 7, Fe, Ru and Os of Group 8, Co, Rh and Ir of Group 9, Ni, Pd and Pt of Group 10, Cu, Ag and Au of Group 11, Zn and Cd of Group 12, Al, Ga, In and Tl of Group 13, Si, Ge, Sn and Pb of Group 14, P, As, Sb and Bi of Group 15, and Se and Te of Group 16. However, the element is by no means limited thereto. Of these elements, the elements of Groups 1, 2, 3, 7, 9, 12, 15 and 16 of the long-form Periodic Table are preferred.

Specific examples of the compound of the element include halides, oxides, carbonates, phosphates, nitrates, sulfates, oxyhalides, basic carbonates, hydroxides, carboxylates and organic metal complexes of the above-described elements. However, the compound of the element is not limited thereto. Among these compounds, halides and oxides are preferred.

Examples of the halogen of the halides or oxyhalides include fluorine, chlorine, bromine and iodine. Of these, chlorine and fluorine are preferred.

The catalyst for use in the present invention may be used in any known form such as liquid or solid and the form is not particularly limited. However, the catalyst is preferably a catalyst of a supported type, a coprecipitated type, an ion exchanged type, a precipitated type, a kneaded type, a melted type, a hydrothermally synthesized type or a gas phase-synthesized type, more preferably a supported type catalyst in which at least one element selected from the elements of Groups 1 to 16 of the long-form Periodic Table or at least one compound containing the at least one element is supported on a support. The element or compound per se may of course be used as a catalyst as it is. Activated carbon is an example of the use of an element as a catalyst as it is.

The at least one element selected from Groups 1 to 16 of the long-form Periodic Table or the compound of the element may suitably be contained in the catalyst in a concentration of from 0.01 to 100 wt %, preferably from 0.1 to 100 wt %, based on the total weight of the catalyst. However, the concentration is not limited thereto.

In the case of a supported catalyst, the support is not particularly limited, and specific examples thereof include single oxides such as alumina, zirconia, titania, niobia, silica and magnesia, composite oxides such as silica-alumina, silica-magnesia and silica-calcia, stratum compounds, zeolite, heteropoly acids, activated carbon, silicon carbide, silicon nitride and polymers. The support may contain the same element as the at least one element selected from the element of Groups 1 to 16 of the long-form Periodic Table to be employed in the catalyst.

The catalyst for use in the present invention can be prepared as described below. For example, in the case of a supported type catalyst obtained by an impregnation process, a compound is dissolved or suspended in an appropriate solvent such as water, alcohol, hydrochloric acid or aqueous ammonia, in an amount such that the support can absorb the solution or suspension. Thereafter, a support having an appropriate particle size is added to the solution or suspension to be impregnated therewith and then dried. The drying may be performed either under atmospheric pressure or a reduced pressure. For example, in the case of drying the catalyst under atmospheric pressure, the support can be dried at from 20 to 300° C. in an air dryer or the like. In the case of drying the catalyst under a reduced pressure, the support can be dried at from 20 to 300° C. in a vacuum dryer or the like. The drying is preferably continued until the catalyst reaches a constant weight.

The dried supported catalyst can be used as it is in the reaction or may be used after being calcined. The calcination may be performed in an atmosphere of nitrogen, carbon dioxide gas, air, oxygen, hydrogen or the like, but the atmosphere is not particularly limited as far as it is matches the purpose. For example, the calcination may be performed in an atmosphere inactive to the compound of at least one element selected from elements of Groups 1 to 16 of the long-form Periodic Table. The calcination is preferably performed in a nitrogen atmosphere.

For the preparation of a catalyst containing an oxide of at least one element selected from elements of Groups 1 to 16 of the long-form Periodic Table, any known method may be used. For example, a catalyst containing a compound of at least one element selected from elements of Groups 1 to 16 of the long-form Periodic Table may be oxidized by calcination in an atmosphere containing an oxidizing agent such as oxygen or air. However, the preparation method is not limited thereto.

For a catalyst containing at least one element selected from elements of Groups 1 to 16 of the long-form Periodic Table, any known preparation method may be used. For example, a catalyst containing a compound of at least one element selected from elements of Groups 1 to 16 of the long-form Periodic Table may be reduced by calcination in an atmosphere containing a reducing agent such as hydrogen, paraffin or an olefin. However, the preparation method is not limited thereto.

The calcination temperature is not particularly limited but may preferably be higher than the reaction temperature.

Also, the calcination time is not particularly limited but the calcination may preferably be performed until the catalyst reaches a constant weight.

For the preparation of a catalyst containing at least two elements selected from elements of Groups 1 to 16 of the long-form Periodic Table or containing compounds of the elements, any known method may be used. For example, in the case where the catalyst is a supported catalyst, the two or more elements or compounds of the elements may be supported in any order. Also, the two or more elements or compounds of the elements may be supported separately or simultaneously. These are not particularly limited.

The shape of the solid catalyst for use in the present invention is not particularly limited and any shape may be used, such as of a tablet, a ring, a sphere, a micro-ball or an extruded article. The shaping may be performed by any known method such as compression molding, extrusion molding and spray dry granulation. Furthermore, the catalyst may be used after being blended with an inactive filler.

The filler for use in the present invention is not particularly limited as long as it is a solid substance, and examples thereof include glass beads, silicon carbide and silicon nitride, however, the present invention is not limited thereto.

Even if the external temperature is constant, reaction may take place in a part of the catalytic layer to cause local heat generation, whereby the temperature may locally be raised. As a result, there may be caused problems such as the increase of by-products and reduction of catalyst life. In such a case, the local heat generation may be inhibited by blending and diluting the catalyst with the above-described filler.

The catalyst and the filler may be blended by any known method such as a method of uniformly blended or a method of varying the blending ratio of the catalyst and the filler in the flowing direction of the reaction gas mixture. Of course, the blending method is by no means limited thereto.

The shape of the filler is not particularly limited and any shape such as a tablet, a ring, a sphere, a micro-ball or an extruded article may be used. Furthermore, the shape may be the same as or different from that of the catalyst.

In the present invention, water may be added at the time of reaction of allyl alcohol with chlorine in a gaseous phase. The water for use in the present invention may be any if it is commercially or industrially available. The water is preferably ion exchanged water, distilled water or the like, however, the present invention is not limited thereto. Also, the water may be previously mixed with allyl alcohol before being added. In particular, it is advantageous to use an azeotropic mixture of water and allyl alcohol as it is. The addition of water is effective in improving the yield of dichloropropanol.

In the present invention, to allow the gas phase reaction to proceed smoothly, conditions are preferably selected so that dichloropropanol (2,3-dichloro-1-propanol (boiling point: 182° C./101 kPa), 1,3-dichloro-2-propanol (boiling point: 174° C./101 kPa)) can be produced in a gas state. On taking account of reaction results, removal of reaction heat, separation of product from raw materials after the reaction, and practical embodiment, it is more preferred to add a diluent.

The diluent for use in the present invention is not particularly limited as long as it does not inhibit the production of dichloropropanol. The diluent is preferably an inert gas. The inert gas is not particularly limited and, for example, nitrogen, carbon dioxide, helium, argon or the like may be used. However, the present invention is not limited thereto. Among these, nitrogen is preferred.

The composition of raw material gas for use in the production of dichloropropanol may preferably be freely selected from the range that allyl alcohol is from 0.01 to 99.99 mol %, chlorine is from 0.00001 to 60 mol %, water is from 0 to 99.99 mol % and the diluent is from 0 to 99.99 mol %.

To allow the gas phase reaction to smoothly proceed, the composition of the raw material gas is preferably selected so that dichloropropanol produced can be maintained in the gas state. In other words, the raw material gas composition is preferably selected so that the partial pressure of dichloropropanol produced can be lower than the saturated vapor pressure of dichloropropanol at the reaction temperature.

The molar ratio of chlorine to allyl alcohol (chlorine/allyl alcohol) used in the present invention may suitably be from 0.001 to 1.5, preferably from 0.01 to 1.2. If the molar ratio of chlorine/allyl alcohol exceeds 1.5, this may cause problems, for example, a side reaction such as displacement reaction may take place due to excess chlorine or a large amount of unreacted chlorine must be recovered. On the other hand, if the molar ratio of chlorine/allyl alcohol is less than 0.001, a large amount of allyl alcohol may have to be disadvantageously recovered.

The molar ratio of water to allyl alcohol (water/allyl alcohol) used in the present invention may suitably be from 0 to 1,000, preferably from 0.0001 to 100, however, the molar ratio is by no means limited thereto.

The molar ratio of diluent to chlorine (diluent/chlorine) used in the present invention may suitably be from 0 to 2,000, preferably from 0 to 1,000, however, the molar ratio is by no means limited thereto.

The raw material gas for use in the production of dichloropropanol of the present invention may suitably flow at a space velocity of from 100 to 120,000 $hr^{-1}$, preferably from 300 to 40,000 $hr^{-1}$, however, the present invention is not limited thereto.

In the process of the present invention, the reaction temperature in the production of dichloropropanol may suitably be from 70 to 300° C., preferably from 80 to 250° C. If the reaction temperature exceeds 300° C., reduction of catalyst life or the like may disadvantageously result due to an increase of a displacement reaction product with chlorine or side production or accumulation of high boiling point compounds. On the other hand, if the reaction temperature is less than 70° C., the amount of diluent used may be increased so as to maintain the gas phase state, as a result, there may cause problems, for example, a large amount of diluent must be recycled, the productivity decreases, or the reaction encounters difficulties in proceeding in a stable gaseous phase.

The heat generated accompanying the reaction of allyl alcohol with chlorine may be eliminated to outside the system using water, warm water or a heating medium, so as to maintain the reaction temperature in a constant range. The heat taken out by water, warm water or a heating medium may be used as a heat source for other facilities and this is beneficial.

In the process of the present invention, the pressure in the production of dichloropropanol may suitably be from 10 to 1,000 kPa, preferably from 50 to 500 kPa. If the reaction pressure is less than 10 kPa or exceeds 1,000 kPa, practice of the process in an industrial scale may be difficult, thus, a reaction pressure outside the above-described range is not preferred.

In practicing the present invention, the reaction system for the gas phase reaction of allyl alcohol with chlorine is not particularly limited and any known reaction system may be used. A continuous flow system may be suitably and preferably used.

The form of the reactor for use in the present invention is not particularly limited but a fixed bed reactor, a fluid bed reaction vessel and the like may be suitably and preferably used.

In the present invention, the raw material gas may be introduced into the reactor by any known method and the introduction method is not particularly limited. For example, allyl alcohol may be introduced by being previously vaporized in a vaporizer. Water may be introduced by being previously vaporized in a vaporizer or may be introduced as a hydrous allyl alcohol after being mixed with allyl alcohol. Chlorine may be introduced together with the previously vaporized allyl alcohol into the reactor or may be introduced separately. More specifically, chlorine may be introduced so that allyl alcohol and chlorine are efficiently brought into contact on a catalyst, as in a method where allyl alcohol and chlorine are previously mixed in a static mixer (see, Kagaku Sochi Chemical Apparatuses), pp.74–78 (May 1994)) and then introduced into a reactor. However, the present invention is by no means limited thereto.

The diluent for use in the present invention may be added to the allyl alcohol, may be added only to the chlorine or may be added to both the allyl alcohol and the chlorine. The addition system is not particularly limited and any known method may be used.

For recovering dichloropropanol from a gas containing dichloropropanol produced in the reactor, any known method may be used. For example, a gas component and a liquid component containing dichloropropanol produced may be separated by cooling the reactor outlet. This liquid component containing dichloropropanol may be subjected to distillation and purification, whereby dichloropropanol may be obtained.

In the case where the diluent used is an inert gas, the inert gas after the separation of dichloropropanol may be recycled or may be purified and then reused. In the case where excess allyl alcohol is used based on chlorine, the liquid component may contain unreacted allyl alcohol depending on the cooling temperature, but this unreacted allyl alcohol may be reused after separating it from dichloropropanol by distillation or the like. It is also possible to condense only dichloropropanol as the desired product by setting the cooling temperature to a high degree and recycling the unreacted allyl alcohol in the gas state as it is or reusing it after purification.

The dichloropropanol produced in the present invention includes 2,3-dichloro-1-propanol and 1,3-dichloro-2-propanol. The dichloropropanol produced has a composition ratio in mol % such that 2,3-dichloro-1-propanol is from 5 to 100 mol % and 1,3-dichloro-1-propanol is from 0 to 95%. These two isomers may be separated by a known method, for example, by rectification or the like. However, the separation method is not limited thereto.

For the production of epichlorohydrin in the second step, dichloropropanol obtained as mentioned above may be used as a starting material without separating those two isomers.

The production of epichlorohydrin may be performed by any known method. For example, similarly to the method described in Japanese Unexamined Patent Publication (Kokai) No. 60-258172, a method of reacting dichloropropanol with an aqueous alkali solution or suspension and thereby producing epichlorohydrin may be preferably used. However, the method is not limited thereto.

The alkaline compound for use in the second step is not particularly limited. For example, an aqueous solution or suspension of calcium hydroxide, sodium hydroxide, potassium hydroxide, sodium carbonate, potassium carbonate or the like may be used, however, the present invention is not limited thereto.

The amount of the alkaline compound used is not particularly limited. The amount of the alkaline compound used is preferably from 1.0 to 1.5 equivalent, more preferably from 1.03 to 1.3 equivalent, per mol of dichloropropanol.

The reaction in the second step may also be performed by any known method. Preferred examples of the method include:

(1) a method of supplying dichloropropanol as the starting material and an aqueous alkali solution or suspension from the top of a plate distillation column, blowing steam from the bottom, and stripping epichlorohydrin produced by the reaction while causing azeotropic distillation (boiling point: 88° C.) with water; in this method, the stripping effect may be increased by allowing an inert gas such as nitrogen to accompany the steam;

(2) a method of mixing dichloropropanol or an aqueous solution with an aqueous alkali solution or suspension in a liquid phase and reacting them while stirring; and (3) a method of allowing the reaction to proceed in the presence of an inactive solvent substantially insoluble in water while extracting epichlorohydrin in the solvent.

In the methods (2) and (3), the reaction may be performed either batchwise or continuously. In the case of continuous reaction, a mixing tank-type reaction or a flow-type reaction in a tower reactor or the like may be used. In the case of a flow-type reaction in a tower reactor, dichloropropanol or a solution thereof and an aqueous alkali solution or suspension may flow cocurrently or countercurrently while coming into contact, to thereby effect reaction. The reaction methods (2) and (3) may be combined, for example, so that the reaction is performed by one method to a certain degree and the reaction is further allowed to proceed according to the other method.

The amount of steam used for the stripping of epichlorohydrin produced in the second step may suitable be such that the top distillate composition has a water/epichlorohydrin ratio by weight of from 0.5 to 3.5, preferably from 1.0 to 2.5. As the amount of steam becomes larger, the selectivity of epichlorohydrin increases. However, if the steam amount is too large, the steam yield may decrease so that the amount used is limited in practice, whereas if the steam amount is too small, the stripping effect may be reduced and the selectivity of epichlorohydrin may decrease.

The reaction temperature in the second step is not particularly limited but it is preferably from 40 to 110° C., more preferably from 60 to 100° C. As the reaction temperature becomes lower, the selectivity of epichlorohydrin increases, however, the reaction rate may decrease and the reaction time may be prolonged.

The reaction pressure in the second step is not particularly limited but it is preferably from 10 to 200 kPa.

The present invention is described in greater detail below by referring to Examples, however, the present invention should not be construed as being limited thereto.

CATALYST PREPARATION PROCESS 1

2.25 g of a compound was dissolved or suspended in 18 g of water, and 42.75 g of a support was added thereto, impregnated with the solution or suspension at room temperature for 30 minutes and then vacuum dried at 150° C. for 3 hours. The dried product was calcined at 200° C. for 3 hours in a nitrogen stream. The catalyst obtained had a composition of a compound (5 wt %)/support (95 wt %).

CATALYST PREPARATION PROCESS 2

2.25 g of a compound was dissolved or suspended in 18 g of methanol, and 42.75 g of a support was added thereto, impregnated with the solution or suspension at room temperature for 30 minutes and then vacuum dried at 150° C. for 3 hours. The dried product was calcined at 200° C. for 3 hours in a nitrogen stream. The catalyst obtained had a composition of a compound (5 wt %)/support (95 wt %).

CATALYST PREPARATION PROCESS 3

2.25 g of a compound was dissolved or suspended in 20 g of 28 wt % aqueous ammonia, and 42.75 g of a support was added thereto, impregnated with the solution or suspension at room temperature for 30 minutes and then vacuum dried at 150° C. for 3 hours. The dried product was calcined at 200° C. for 3 hours in a nitrogen stream. The catalyst obtained had a composition of a compound (5 wt %)/support (95 wt %).

CATALYST PREPARATION PROCESS 4

A compound in an amount corresponding to 2.25 g of an oxide was dissolved or suspended in 18 g of water, and 42.75 g of a support was added thereto, impregnated with the solution or suspension at room temperature for 30 minutes, evaporated to dryness on a water bath and then air dried at 120° C. for 12 hours. The dried product was calcined at 500° C. for 3 hours in an air stream. The catalyst obtained had an composition of an oxide (5 wt %)/support (95 wt %).

CATALYST PREPARATION PROCESS 5

2.25 g of Compound A and Compound B in an amount equimolar to 2.25 g of Compound A were dissolved or suspended in 18 g of water, and 42.75 g of a support was added thereto, impregnated with the solution or suspension at room temperature for 30 minutes and then vacuum dried at 150° C. for 3 hours. The dried product was calcined at 200° C. for 3 hours in a nitrogen stream. The catalyst obtained had a composition of Compound A+Compound B/support.

CATALYST PREPARATION PROCESS 6

2.25 g of Compound A and Compound B in an amount equimolar to 2.25 g of Compound A were dissolved or suspended in 18 g of methanol, and 42.75 g of a support was added thereto, impregnated with the solution or suspension at room temperature for 30 minutes and then vacuum dried at 150° C. for 3 hours. The dried product was calcined at 200° C. for 3 hours in a nitrogen stream. The catalyst obtained had a composition of Compound A+Compound B/support.

CATALYST PREPARATION PROCESS 7

2.25 g of Compound A and Compound B in an amount equimolar to 2.25 g of Compound A were dissolved or suspended in 20 g of 28 wt % aqueous ammonia, and 42.75 g of a support was added thereto, impregnated with the solution or suspension at room temperature for 30 minutes and then vacuum dried at 150° C. for 3 hours. The dried product was calcined at 200° C. for 3 hours in a nitrogen stream. The catalyst obtained had a composition of Compound A+Compound B/support.

CATALYST PREPARATION PROCESS 8

2.25 g of Compound A and Compound B in an amount equimolar to 2.25 g of Compound A were dissolved or suspended in 18 g of 2 mol/l of hydrochloric acid, and 42.75 g of a support was added thereto, impregnated with the solution or suspension at room temperature for 30 minutes and then vacuum dried at 150° C. for 3 hours. The dried product was calcined at 200° C. for 3 hours in a nitrogen stream. The catalyst obtained had a composition of Compound A+Compound B/support.

CATALYST PREPARATION PROCESS 9

2.25 g of Compound A, Compound B in an amount equimolar to 2.25 g of Compound A and Compound C at 0.5 mol equivalent to 2.25 g of Compound A were dissolved or suspended in 18 g of water, and 42.75 g of a support was added thereto, impregnated with the solution or suspension at room temperature for 30 minutes and then vacuum dried at 150° C. for 3 hours. The dried product was calcined at 200° C. for 3 hours in a nitrogen stream. The catalyst obtained had a composition of Compound A+Compound B+Compound C/support.

CATALYST PREPARATION PROCESS 10

2.25 g of Compound A and Compound B in an amount equimolar to 2.25 g of Compound A and Compound C at 0.5 mol equivalent to 2.25 g of Compound A were dissolved or suspended in 18 g of methanol, and 42.75 g of a support was added thereto, impregnated with the solution or suspension at room temperature for 30 minutes and then vacuum dried at 150° C. for 3 hours. The dried product was calcined at 200° C. for 3 hours in a nitrogen stream. The catalyst obtained had a composition of Compound A+Compound B+Compound C/support.

EXAMPLE 1

A catalyst was prepared using LiCl as the compound and $Al_2O_3$ (particle size: 1.6 mm) as the support according to Catalyst Preparation Process 1.

16 ml of the catalyst was filled in a vertical glass-made reactor having an internal diameter of 14 mm and a length of 15 cm equipped with a glass tube for the measurement of temperature.

The reactor was heated to 140° C. by a heating medium and into the reactor, a raw material gas comprising 1.3 mol % of chlorine, 3.3 mol % of allyl alcohol, 4.6 mol % of water and 90.8 mol % of nitrogen was introduced under atmospheric pressure and at a space velocity of 4,131 $h^{-1}$, and reacted. The allyl alcohol and water were each previously vaporized through a vaporizer set at 140° C.

Thereafter, the outlet of the reactor was cooled and a condensed distillate was recovered. The distillate obtained was analyzed by high-performance liquid chromatography to determine the yield of dichloropropanol (based on the raw material chlorine) and the composition ratio (mol %) thereof. Also, the maximum temperature of the catalyst layer in the reactor was measured as the reaction temperature. The results are shown in Table 1.

EXAMPLE 2

A reaction was performed in the same manner as in Example 1 except that the compound was NaCl. The results are shown in Table 1.

EXAMPLE 3

A reaction was performed in the same manner as in Example 1 except that the compound was KCl. The results are shown in Table 1.

EXAMPLE 4

A reaction was performed in the same manner as in Example 1 except that the compound was RbCl. The results are shown in Table 1.

EXAMPLE 5

A reaction was performed in the same manner as in Example 1 except that the compound was CsCl. The results are shown in Table 1.

EXAMPLE 6

A reaction was performed in the same manner as in Example 1 except that the compound was $BeCl_2$. The results are shown in Table 1.

EXAMPLE 7

A reaction was performed in the same manner as in Example 1 except that the compound was $MgCl_2$. The results are shown in Table 1.

EXAMPLE 8

A reaction was performed in the same manner as in Example 1 except that the compound was $CaCl_2$. The results are shown in Table 1.

EXAMPLE 9

A reaction was performed in the same manner as in Example 1 except that the compound was $SrCl_2$. The results are shown in Table 1.

EXAMPLE 10

A reaction was performed in the same manner as in Example 1 except that the compound was $BaCl_2$. The results are shown in Table 1.

EXAMPLE 11

A reaction was performed in the same manner as in Example 1 except that the compound was $YCl_3$. The results are shown in Table 1.

EXAMPLE 12

A reaction was performed in the same manner as in Example 1 except that the compound was $ScCl_3$. The results are shown in Table 1.

EXAMPLE 13

A reaction was performed in the same manner as in Example 1 except that the compound was $LaCl_3$. The results are shown in Table 1.

EXAMPLE 14

A reaction was performed in the same manner as in Example 1 except that the compound was $TiCl_3$. The results are shown in Table 1.

EXAMPLE 15

A reaction was performed in the same manner as in Example 1 except that the compound was $VCl_3$ and the catalyst was prepared according to Catalyst Preparation Process 2. The results are shown in Table 1.

EXAMPLE 16

A reaction was performed in the same manner as in Example 1 except that the compound was $CrCl_2$ and the catalyst was prepared according to Catalyst Preparation Process 2. The results are shown in Table 2.

EXAMPLE 17

A reaction was performed in the same manner as in Example 1 except that the compound was $WCl_6$ and the catalyst was prepared according to Catalyst Preparation Process 2. The results are shown in Table 2.

EXAMPLE 18

A reaction was performed in the same manner as in Example 1 except that the compound was $MnCl_2$ and the catalyst was prepared according to Catalyst Preparation Process 2. The results are shown in Table 2.

EXAMPLE 19

A reaction was performed in the same manner as in Example 1 except that the compound was $ReCl_3$ and the catalyst was prepared according to Catalyst Preparation Process 2. The results are shown in Table 2.

EXAMPLE 20

A reaction was performed in the same manner as in Example 1 except that the compound was $FeCl_2$ and the catalyst was prepared according to Catalyst Preparation Process 2. The results are shown in Table 2.

EXAMPLE 21

A reaction was performed in the same manner as in Example 1 except that the compound was $FeCl_3$ and the catalyst was prepared according to Catalyst Preparation Process 2. The results are shown in Table 2.

EXAMPLE 22

A reaction was performed in the same manner as in Example 1 except that the compound was $RuCl_3$ and the catalyst was prepared according to Catalyst Preparation Process 2. The results are shown in Table 2.

EXAMPLE 23

A reaction was performed in the same manner as in Example 1 except that the compound was $CoCl_2$ and the catalyst was prepared according to Catalyst Preparation Process 2. The results are shown in Table 2.

EXAMPLE 24

A reaction was performed in the same manner as in Example 1 except that the compound was $RhCl_3$ and the catalyst was prepared according to Catalyst Preparation Process 2. The results are shown in Table 2.

EXAMPLE 25

A reaction was performed in the same manner as in Example 1 except that the compound was $NiCl_2$. The results are shown in Table 2.

EXAMPLE 26

A reaction was performed in the same manner as in Example 1 except that the compound was $PdCl_2$ and the catalyst was prepared according to Catalyst Preparation Process 3. The results are shown in Table 2.

EXAMPLE 27

A reaction was performed in the same manner as in Example 1 except that the compound was $H_2PtCl_4$. The results are shown in Table 2.

EXAMPLE 28

A reaction was performed in the same manner as in Example 1 except that the compound was CuCl and the catalyst was prepared according to Catalyst Preparation Process 3. The results are shown in Table 2.

EXAMPLE 29

A reaction was performed in the same manner as in Example 1 except that the compound was $CuCl_2$ and the catalyst was prepared according to Catalyst Preparation Process 2. The results are shown in Table 2.

EXAMPLE 30

A reaction was performed in the same manner as in Example 1 except that the compound was AgCl and the catalyst was prepared according to Catalyst Preparation Process 3. The results are shown in Table 2.

EXAMPLE 31

A reaction was performed in the same manner as in Example 1 except that the compound was $ZnCl_2$ and the catalyst was prepared according to Catalyst Preparation Process 2. The results are shown in Table 3.

EXAMPLE 32

A reaction was performed in the same manner as in Example 1 except that the compound was $ZnF_2$ and the catalyst was prepared according to Catalyst Preparation Process 3. The results are shown in Table 3.

EXAMPLE 33

A reaction was performed in the same manner as in Example 1 except that the compound was $ZnBr_2$ and the catalyst was prepared according to Catalyst Preparation Process 2. The results are shown in Table 3.

EXAMPLE 34

A reaction was performed in the same manner as in Example 1 except that the compound was $ZnI_2$ and the catalyst was prepared according to Catalyst Preparation Process 2. The results are shown in Table 3.

EXAMPLE 35

A reaction was performed in the same manner as in Example 1 except that 8.23 g of $Zn(NO_3)_2 \cdot 6H_2O$ was used as the compound and the catalyst (ZnO (5 wt %)/$Al_2O_3$ (95 wt %)) was prepared according to Catalyst Preparation Process 4. The results are shown in Table 3.

EXAMPLE 36

A reaction was performed in the same manner as in Example 1 except that the compound was $ZnSO_4$ and the catalyst was prepared according to Catalyst Preparation Process 1. The results are shown in Table 3.

EXAMPLE 37

A reaction was performed in the same manner as in Example 1 except that the compound was $Zn_3(PO_4)_2$ and the catalyst was prepared according to Catalyst Preparation Process 3. The results are shown in Table 3.

EXAMPLE 38

A reaction was performed in the same manner as in Example 1 except that 8.81 g of $Ga(NO_3)_3$ hydrate (Ga content: 19 wt %) was used as the compound and the catalyst ($Ga_2O_3$ (5 wt %)/$Al_2O_3$ (95 wt %)) was prepared according to Catalyst Preparation Process 4. The results are shown in Table 3.

EXAMPLE 39

A reaction was performed in the same manner as in Example 1 except that the compound was $InCl_3$. The results are shown in Table 3.

EXAMPLE 40

A reaction was performed in the same manner as in Example 1 except that the compound was $SnCl_2$ and the catalyst was prepared according to Catalyst Preparation Process 2. The results are shown in Table 3.

EXAMPLE 41

A reaction was performed in the same manner as in Example 1 except that the catalyst was prepared using $PbCl_2$ as the compound by dissolving it in 120 g of water according to Catalyst Preparation Process 1. The results are shown in Table 3.

EXAMPLE 42

A reaction was performed in the same manner as in Example 1 except that 3.34 g of $Pb(NO_3)_2$ was used as the compound and the catalyst (PbO (5 wt %)/$Al_2O_3$ (95 wt %)) was prepared according to Catalyst Preparation Process 4. The results are shown in Table 3.

EXAMPLE 43

A reaction was performed in the same manner as in Example 1 except that the compound was $Sb_2O_5$ and the catalyst was prepared according to Catalyst Preparation Process 1. The results are shown in Table 3.

EXAMPLE 44

A reaction was performed in the same manner as in Example 1 except that the compound was $BiCl_3$ and the catalyst was prepared according to Catalyst Preparation Process 2. The results are shown in Table 3.

EXAMPLE 45

A reaction was performed in the same manner as in Example 1 except that the catalyst was $Al_2O_3$ (particle size: 1.6 mm). The results are shown in Table 3.

EXAMPLE 46

A reaction was performed in the same manner as in Example 1 except that the catalyst was $ZrO_2$ (particle size: 0.5 to 2.0 mm). The results are shown in Table 4.

EXAMPLE 47

A reaction was performed in the same manner as in Example 1 except that the catalyst was $Nb_2O_5$ (particle size: 0.5 to 2.0 mm). The results are shown in Table 4.

EXAMPLE 48

A reaction was performed in the same manner as in Example 1 except that the catalyst was $TiO_2$ (particle size: 0.5 to 2.0 mm). The results are shown in Table 4.

EXAMPLE 49

A reaction was performed in the same manner as in Example 31 except that the reactor was heated to 110° C. by a heating medium and the vaporizer was set at 110° C. The results are shown in Table 4.

EXAMPLE 50

A reaction was performed in the same manner as in Example 31 except that the reactor was heated to 130° C. by a heating medium and the vaporizer was set at 130° C. The results are shown in Table 4.

EXAMPLE 51

A reaction was performed in the same manner as in Example 1 except that a catalyst prepared using $ZnCl_2$ as the compound and $Al_2O_3$ (particle size: 1.6 mm) as the support according to Catalyst Preparation Process 2 was filled in a reactor and a raw material gas comprising 1.3 mol % of chlorine, 3.3 mol % of allyl alcohol and 95.4 mol % of nitrogen was introduced into the reactor at a space velocity of 4,131 $h^{-1}$. The results are shown in Table 4.

EXAMPLE 52

A reaction was performed in the same manner as in Example 1 except that a catalyst prepared using $ZnCl_2$ as the compound and $Al_2O_3$ (particle size: 1.6 mm) as the support according to Catalyst Preparation Process 2 was filled in a reactor and a raw material gas comprising 1.3 mol % of chlorine and 98.7 mol % of allyl alcohol was introduced into the reactor at a space velocity of 4,131 $h^{-1}$. The results are shown in Table 4.

EXAMPLE 53

A reaction was performed in the same manner as in Example 1 except that Compound A was $ZnCl_2$, Compound B was LiCl, the support was $Al_2O_3$ (particle size: 1.6 mm) and the catalyst was prepared according to Catalyst Preparation Process 5. The results are shown in Table 4.

EXAMPLE 54

A reaction was performed in the same manner as in Example 1 except that Compound A was $ZnCl_2$, Compound B was NaCl, the support was $Al_2O_3$ (particle size: 1.6 mm) and the catalyst was prepared according to Catalyst Preparation Process 5. The results are shown in Table 4.

EXAMPLE 55

A reaction was performed in the same manner as in Example 1 except that Compound A was $ZnCl_2$, Compound B was KCl, the support was $Al_2O_3$ (particle size: 1.6 mm) and the catalyst was prepared according to Catalyst Preparation Process 5. The results are shown in Table 4.

EXAMPLE 56

A reaction was performed in the same manner as in Example 1 except that Compound A was $ZnCl_2$, Compound B was RbCl, the support was $Al_2O_3$ (particle size: 1.6 mm) and the catalyst was prepared according to Catalyst Preparation Process 5. The results are shown in Table 4.

EXAMPLE 57

A reaction was performed in the same manner as in Example 1 except that Compound A was $ZnCl_2$, Compound B was CsCl, the support was $Al_2O_3$ (particle size: 1.6 mm) and the catalyst was prepared according to Catalyst Preparation Process 5. The results are shown in Table 4.

EXAMPLE 58

A reaction was performed in the same manner as in Example 1 except that Compound A was $ZnCl_2$, Compound B was $BeCl_2$, the support was $Al_2O_3$ (particle size: 1.6 mm) and the catalyst was prepared according to Catalyst Preparation Process 5. The results are shown in Table 4.

EXAMPLE 59

A reaction was performed in the same manner as in Example 1 except that Compound A was $ZnCl_2$, Compound B was $MgCl_2$, the support was $Al_2O_3$ (particle size: 1.6 mm) and the catalyst was prepared according to Catalyst Preparation Process 5. The results are shown in Table 4.

EXAMPLE 60

A reaction was performed in the same manner as in Example 1 except that Compound A was $ZnCl_2$, Compound B was $CaCl_2$, the support was $Al_2O_3$ (particle size: 1.6 mm) and the catalyst was prepared according to Catalyst Preparation Process 5. The results are shown in Table 4.

EXAMPLE 61

A reaction was performed in the same manner as in Example 1 except that Compound A was $ZnCl_2$, Compound B was $SrCl_2$, the support was $Al_2O_3$ (particle size: 1.6 mm) and the catalyst was prepared according to Catalyst Preparation Process 5. The results are shown in Table 5.

EXAMPLE 62

A reaction was performed in the same manner as in Example 1 except that Compound A was $ZnCl_2$ Compound B was $BaCl_2$, the support was $Al_2O_3$ (particle size: 1.6 mm) and the catalyst was prepared according to Catalyst Preparation Process 5. The results are shown in Table 5.

EXAMPLE 63

A reaction was performed in the same manner as in Example 1 except that Compound A was $ZnCl_2$, Compound B was $YCl_3$, the support was $Al_2O_3$ (particle size: 1.6 mm) and the catalyst was prepared according to Catalyst Preparation Process 5. The results are shown in Table 5.

EXAMPLE 64

A reaction was performed in the same manner as in Example 1 except that Compound A was $ZnCl_2$, Compound B was $ScCl_3$, the support was $Al_2O_3$ (particle size: 1.6 mm) and the catalyst was prepared according to Catalyst Preparation Process 5. The results are shown in Table 5.

EXAMPLE 65

A reaction was performed in the same manner as in Example 1 except that Compound A was $ZnCl_2$, Compound B was $LaCl_3$, the support was $Al_2O_3$ (particle size: 1.6 mm) and the catalyst was prepared according to Catalyst Preparation Process 5. The results are shown in Table 5.

EXAMPLE 66

A reaction was performed in the same manner as in Example 1 except that Compound A was $ZnCl_2$, Compound B was $TiCl_3$, the support was $Al_2O_3$ (particle size: 1.6 mm) and the catalyst was prepared according to Catalyst Preparation Process 5. The results are shown in Table 5.

EXAMPLE 67

A reaction was performed in the same manner as in Example 1 except that Compound A was $ZnCl_2$, Compound B was $VCl_3$, the support was $Al_2O_3$ (particle size: 1.6 mm) and the catalyst was prepared according to Catalyst Preparation Process 6. The results are shown in Table 5.

EXAMPLE 68

A reaction was performed in the same manner as in Example 1 except that Compound A was $ZnCl_2$, Compound B was $CrCl_2$, the support was $Al_2O_3$ (particle size: 1.6 mm) and the catalyst was prepared according to Catalyst Preparation Process 6. The results are shown in Table 5.

EXAMPLE 69

A reaction was performed in the same manner as in Example 1 except that Compound A was $ZnCl_2$, Compound B was $WCl_6$, the support was $Al_2O_3$ (particle size: 1.6 mm) and the catalyst was prepared according to Catalyst Preparation Process 6. The results are shown in Table 5.

EXAMPLE 70

A reaction was performed in the same manner as in Example 1 except that Compound A was $ZnCl_2$, Compound B was $MnCl_2$, the support was $Al_2O_3$ (particle size: 1.6 mm) and the catalyst was prepared according to Catalyst Preparation Process 6. The results are shown in Table 5.

EXAMPLE 71

A reaction was performed in the same manner as in Example 1 except that Compound A was $ZnCl_2$, Compound B was $ReCl_3$, the support was $Al_2O_3$ (particle size: 1.6 mm) and the catalyst was prepared according to Catalyst Preparation Process 6. The results are shown in Table 5.

EXAMPLE 72

A reaction was performed in the same manner as in Example 1 except that Compound A was $ZnCl_2$, Compound B was $FeCl_2$, the support was $Al_2O_3$ (particle size: 1.6 mm) and the catalyst was prepared according to Catalyst Preparation Process 6. The results are shown in Table 5.

EXAMPLE 73

A reaction was performed in the same manner as in Example 1 except that Compound A was $ZnCl_2$, Compound B was $FeCl_3$, the support was $Al_2O_3$ (particle size: 1.6 mm) and the catalyst was prepared according to Catalyst Preparation Process 6. The results are shown in Table 5.

EXAMPLE 74

A reaction was performed in the same manner as in Example 1 except that Compound A was $ZnCl_2$, Compound B was $RuCl_3$, the support was $Al_2O_3$ (particle size: 1.6 mm) and the catalyst was prepared according to Catalyst Preparation Process 6. The results are shown in Table 5.

EXAMPLE 75

A reaction was performed in the same manner as in Example 1 except that Compound A was $ZnCl_2$, Compound B was COCl$_2$, the support was Al$_2$O$_3$ (particle size: 1.6 mm) and the catalyst was prepared according to Catalyst Preparation Process 6. The results are shown in Table 5.

EXAMPLE 76

A reaction was performed in the same manner as in Example 1 except that Compound A was ZnCl$_2$, Compound B was RhCl$_3$, the support was Al$_2$O$_3$ (particle size: 1.6 mm) and the catalyst was prepared according to Catalyst Preparation Process 6. The results are shown in Table 6.

EXAMPLE 77

A reaction was performed in the same manner as in Example 1 except that Compound A was ZnCl$_2$, Compound B was NiCl$_2$, the support was Al$_2$O$_3$ (particle size: 1.6 mm) and the catalyst was prepared according to Catalyst Preparation Process 5. The results are shown in Table 6.

EXAMPLE 78

A reaction was performed in the same manner as in Example 1 except that Compound A was ZnCl$_2$, Compound B was PdCl$_2$, the support was Al$_2$O$_3$ (particle size: 1.6 mm) and the catalyst was prepared according to Catalyst Preparation Process 7. The results are shown in Table 6.

EXAMPLE 79

A reaction was performed in the same manner as in Example 1 except that Compound A was ZnCl$_2$, Compound B was H$_2$PtCl$_4$, the support was Al$_2$O$_3$ (particle size: 1.6 mm) and the catalyst was prepared according to Catalyst Preparation Process 5. The results are shown in Table 6.

EXAMPLE 80

A reaction was performed in the same manner as in Example 1 except that Compound A was ZnCl$_2$, Compound B was CuCl, the support was Al$_2$O$_3$ (particle size: 1.6 mm) and the catalyst was prepared according to Catalyst Preparation Process 7. The results are shown in Table 6.

EXAMPLE 81

A reaction was performed in the same manner as in Example 1 except that Compound A was ZnCl$_2$, Compound B was CuCl$_2$, the support was Al$_2$O$_3$ (particle size: 1.6 mm) and the catalyst was prepared according to Catalyst Preparation Process 6. The results are shown in Table 6.

EXAMPLE 82

A reaction was performed in the same manner as in Example 1 except that Compound A was ZnCl$_2$, Compound B was AgCl, the support was Al$_2$O$_3$ (particle size: 1.6 mm) and the catalyst was prepared according to Catalyst Preparation Process 7. The results are shown in Table 6.

EXAMPLE 83

A reaction was performed in the same manner as in Example 1 except that Compound A was ZnCl$_2$, Compound B was InCl$_3$, the support was Al$_2$O$_3$ (particle size: 1.6 mm) and the catalyst was prepared according to Catalyst Preparation Process 5. The results are shown in Table 6.

EXAMPLE 84

A reaction was performed in the same manner as in Example 1 except that Compound A was ZnCl$_2$, Compound B was SnCl$_2$, the support was Al$_2$O$_3$ (particle size: 1.6 mm) and the catalyst was prepared according to Catalyst Preparation Process 5. The results are shown in Table 6.

EXAMPLE 85

A reaction was performed in the same manner as in Example 1 except that Compound A was ZnCl$_2$, Compound B was PbCl$_2$, the support was Al$_2$O$_3$ (particle size: 1.6 mm) and the catalyst was prepared according to Catalyst Preparation Process 5. The results are shown in Table 6.

EXAMPLE 86

A reaction was performed in the same manner as in Example 1 except that Compound A was ZnCl$_2$, Compound B was Sb$_2$O$_5$, the support was Al$_2$O$_3$ (particle size: 1.6 mm) and the catalyst was prepared according to Catalyst Preparation Process 5. The results are shown in Table 6.

EXAMPLE 87

A reaction was performed in the same manner as in Example 1 except that Compound A was ZnCl$_2$, Compound B was BiCl$_3$, the support was Al$_2$O$_3$ (particle size: 1.6 mm) and the catalyst was prepared according to Catalyst Preparation Process 6. The results are shown in Table 6.

EXAMPLE 88

A reaction was performed in the same manner as in Example 1 except that Compound A was MgCl$_2$, Compound B was CaCl$_2$, the support was Al$_2$O$_3$ (particle size: 1.6 mm) and the catalyst was prepared according to Catalyst Preparation Process 5. The results are shown in Table 6.

EXAMPLE 89

A reaction was performed in the same manner as in Example 1 except that Compound A was InCl$_3$, Compound B was BaCl$_2$, the support was Al$_2$O$_3$ (particle size: 1.6 mm) and the catalyst was prepared according to Catalyst Preparation Process 5. The results are shown in Table 6.

EXAMPLE 90

A reaction was performed in the same manner as in Example 1 except that Compound A was ZnCl$_2$, Compound B was MgCl$_2$, the support was ZrO$_2$ (particle size: 0.5 to 2.0 mm) and the catalyst was prepared according to Catalyst Preparation Process 5. The results are shown in Table 6.

EXAMPLE 91

A reaction was performed in the same manner as in Example 1 except that Compound A was ZnCl$_2$, Compound B was MgCl$_2$, the support was TiO$_2$ (particle size: 0.5 to 2.0 mm) and the catalyst was prepared according to Catalyst Preparation Process 5. The results are shown in Table 7.

EXAMPLE 92

A reaction was performed in the same manner as in Example 1 except that Compound A was ZnCl$_2$, Compound B was MgCl$_2$, the support was SiO$_2$ (particle size: 0.5 to 2.0 mm) and the catalyst was prepared according to Catalyst Preparation Process 5. The results are shown in Table 7.

EXAMPLE 93

A reaction was performed in the same manner as in Example 1 except that Compound A was ZnCl$_2$, Compound B was $MgCl_2$, the support was SiC (particle size: 1.0 to 2.0 mm) and the catalyst was prepared according to Catalyst Preparation Process 5. The results are shown in Table 7.

EXAMPLE 94

A reaction was performed in the same manner as in Example 1 except that a catalyst prepared using $ZnCl_2$ as Compound A, $MgCl_2$ as Compound B and $Al_2O_3$ (particle size: 1.6 mm) as the support according to Catalyst Preparation Process 5 was filled in a reactor and a raw material gas comprising 1.3 mol % of chlorine, 3.3 mol % of allyl alcohol and 95.4 mol % of nitrogen was introduced into the reactor at a space velocity of 4,131 $h^{-1}$. The results are shown in Table 7.

EXAMPLE 95

A reaction was performed in the same manner as in Example 1 except that a catalyst prepared using $ZnCl_2$ as Compound A, $MgCl_2$ as Compound B and $Al_2O_3$ (particle size: 1.6 mm) as the support according to Catalyst Preparation Process 5 was filled in a reactor and a raw material gas comprising 4.8 mol % of chlorine, 5.3 mol % of allyl alcohol, 7.4 mol % of water and 82.5 mol % of nitrogen was introduced into the reactor at a space velocity of 1,137 $h^{-1}$. The results are shown in Table 7.

EXAMPLE 96

A reaction was performed in the same manner as in Example 1 except that a catalyst prepared using $ZnCl_2$ as Compound A, $MgCl_2$ as Compound B and $Al_2O_3$ (particle size: 1.6 mm) as the support according to Catalyst Preparation Process 5 was filled in a reactor and a raw material gas comprising 4.8 mol % of chlorine, 5.3 mol % of allyl alcohol, 48.0 mol % of water and 41.9 mol % of nitrogen was introduced into the reactor at a space velocity of 1,137 $h^{-1}$. The results are shown in Table 7.

EXAMPLE 97

A reaction was performed in the same manner as in Example 1 except that a catalyst prepared using $ZnCl_2$ as Compound A, $MgCl_2$ as Compound B and $Al_2O_3$ (particle size: 1.6 mm) as the support according to Catalyst Preparation Process 5 was filled in a reactor and a raw material gas comprising 4.8 mol % of chlorine, 5.3 mol % of allyl alcohol and 89.9 mol % of water was introduced into the reactor at a space velocity of 1,137 $h^{-1}$. The results are shown in Table 7.

EXAMPLE 98

A reaction was performed in the same manner as in Example 1 except that 5.3 ml of a catalyst prepared using $ZnCl_2$ as Compound A, $MgCl_2$ as Compound B and $Al_2O_3$ (particle size: 1.6 mm) as the support according to Catalyst Preparation Process 5 and 10.7 ml of glass beads (particle size: 0.99 to 1.4 mm) as a filler were mixed to form a homogeneous mixture as much as possible and filled in a reactor and a raw material gas comprising 4.8 mol % of chlorine, 5.3 mol % of allyl alcohol, 7.4 mol % of water and 82.5 mol % of nitrogen was introduced into the reactor based on the catalyst and filler (total: 16 ml) at a space velocity of 1,137 $h^{-1}$. The results are shown in Table 7.

EXAMPLE 99

A reaction was performed in the same manner as in Example 98 except that 10.7 ml of silicon carbide (particle size: 2.0 mm) was used as the filler. The results are shown in Table 7.

EXAMPLE 100

A reaction was performed in the same manner as in Example 1 except that a catalyst was not filled in the reactor. The results are shown in Table 7.

EXAMPLE 101

A reaction was performed in the same manner as in Example 1 except that the compound was $TeCl_4$ and the catalyst was prepared according to Catalyst Preparation Process 2. The results are shown in Table 7.

EXAMPLE 102

A reaction was performed in the same manner as in Example 1 except that Compound A was $ZnCl_2$, Compound B was $TeCl_4$, the support was $Al_2O_3$ (particle size: 1.6 mm) and the catalyst was prepared according to Catalyst Preparation Process 6. The results are shown in Table 7.

EXAMPLE 103

A reaction was performed in the same manner as in Example 1 except that Compound A was $ZnCl_2$, Compound B was $MgCl_2$, the support was $Al_2O_3$ (particle size: 1.6 mm) and the catalyst was prepared according to Catalyst Preparation Process 8. The results are shown in Table 7.

EXAMPLE 104

A reaction was performed in the same manner as in Example 1 except that the catalyst was activated carbon (particle size: 0.5 to 2.0 mm). The results are shown in Table 7.

EXAMPLE 105

A reaction was performed in the same manner as in Example 1 except that Compound A was $ZnCl_2$, Compound B was $MgCl_2$, Compound C was NaCl, the support was $Al_2O_3$ (particle size: 1.6 mm) and the catalyst was prepared according to Catalyst Preparation Process 9. The results are shown in Table 8.

EXAMPLE 106

A reaction was performed in the same manner as in Example 1 except that Compound A was $ZnCl_2$, Compound B was $MgCl_2$, Compound C was $CaCl_2$, the support was $Al_2O_3$ (particle size: 1.6 mm) and the catalyst was prepared according to Catalyst Preparation Process 9. The results are shown in Table 8.

EXAMPLE 107

A reaction was performed in the same manner as in Example 1 except that Compound A was $ZnCl_2$, Compound B was $MgCl_2$, Compound C was $SrCl_2$, the support was $Al_2O_3$ (particle size: 1.6 mm) and the catalyst was prepared according to Catalyst Preparation Process 9. The results are shown in Table 8.

EXAMPLE 108

A reaction was performed in the same manner as in Example 1 except that Compound A was $ZnCl_2$, Compound B was $MgCl_2$, Compound C was $YCl_3$, the support was $Al_2O_3$ (particle size: 1.6 mm) and the catalyst was prepared according to Catalyst Preparation Process 9. The results are shown in Table 8.

EXAMPLE 109

A reaction was performed in the same manner as in Example 1 except that Compound A was $ZnCl_2$, Compound B was MgCl$_2$, Compound C was MnCl$_2$, the support was Al$_2$O$_3$ (particle size: 1.6 mm) and the catalyst was prepared according to Catalyst Preparation Process 10. The results are shown in Table 8.

EXAMPLE 110

A reaction was performed in the same manner as in Example 1 except that Compound A was ZnCl$_2$, Compound B was MgCl$_2$, Compound C was CoCl$_2$, the support was Al$_2$O$_3$ (particle size: 1.6 mm) and the catalyst was prepared according to Catalyst Preparation Process 10. The results are shown in Table 8.

EXAMPLE 111

A reaction was performed in the same manner as in Example 1 except that Compound A was ZnCl$_2$, Compound B was MgCl$_2$, Compound C was BiCl$_3$, the support was Al$_2$O$_3$ (particle size: 1.6 mm) and the catalyst was prepared according to Catalyst Preparation Process 10. The results are shown in Table 8.

EXAMPLE 112

A reaction was performed in the same manner as in Example 1 except that Compound A was ZnCl$_2$, Compound B was MgCl$_2$, Compound C was TeCl$_4$, the support was Al$_2$O$_3$ (particle size: 1.6 mm) and the catalyst was prepared according to Catalyst Preparation Process 10. The results are shown in Table 8.

EXAMPLE 113

Production of Epichlorohydrin

The following dehydrochlorination column was used for performing dehydrochlorination reaction of dichloropropanol and for stripping to immediately separate epichlorohydrin produced from the reaction liquid.

The dehydrochlorinating column body was made of glass and had an inner diameter of 55 mmϕ and a height of 1,500 mm. In the column, 10 porous plates each having thereon 280 holes of 1 mm diameter were disposed at an interval of 100 mm and each porous plate had a downcomer of a depth of 5 mm. At the lower side of the lowermost plate, a steam blowing nozzle was disposed to feed a constant amount of steam through a flowmeter. At the upper side of the uppermost plate, a liquid feed nozzle was disposed to feed dichloropropanol and an aqueous alkali solution. The dichloropropanol solution and the aqueous alkali solution were delivered by a metering pump and mixed immediately before the liquid feed nozzle. From the column top, the distillate is recovered through a condenser. At the column bottom, a 500 ml round bottom flask was fixed and the bottom liquid was extracted in a constant amount by a metering pump to keep the bottom amount of 40 ml.

Using the above-described apparatus, the dichloropropanol obtained in Example 59 and an aqueous solution of 9.5 wt % Ca(OH)$_2$ slurry were fed through the liquid feed nozzle at a rate of 83 g/h and 323 g/h, respectively. At the same time, steam was blown through the steam blowing nozzle. The concentration of dichloropropanol during the feeding was 20 wt %. While extracting the waste solution from the column bottom, the operation was continued for about 2 hours until the reaction system was stabilized. After 1 hour, the top distillate and the bottom solution were sampled and the compositions were analyzed. As a result, the conversion of dichloropropanol was 89.1% and the selectivity of epichlorohydrin was 97.0%. The temperature in the middle column was 100° C.

EXAMPLE 114

A reaction was performed in the same manner as in Example 113 except that the dichloropropanol obtained in Example 99 was used. As a result, the conversion of dichloropropanol was 90.2% and the selectivity of epichlorohydrin was 96.8%. The temperature in the middle column was 99° C.

TABLE 1

| Example | Catalyst (wt %) | Reaction Temperature (° C.) | Yield of Dichloropropanol (%) | Composition Ratio (mol %) | |
|---|---|---|---|---|---|
| | | | | 2,3-Dichloro-1-propanol | 1,3-Dichloro-2-propanol |
| 1 | LiCl(5)/Al$_2$O$_3$(95) | 155 | 73.8 | 97.5 | 2.5 |
| 2 | NaCl(5)/Al$_2$O$_3$(95) | 159 | 68.1 | 95.1 | 4.9 |
| 3 | KCl(5)/Al$_2$O$_3$(95) | 153 | 72.2 | 96.1 | 3.9 |
| 4 | RbCl(5)/Al$_2$O$_3$(95) | 155 | 71.4 | 98.0 | 2.0 |
| 5 | CsCl(5)/Al$_2$O$_3$(95) | 153 | 74.7 | 96.9 | 3.1 |
| 6 | BeCl$_2$(5)/Al$_2$O$_3$(95) | 157 | 78.9 | 97.3 | 2.7 |
| 7 | MgCl$_2$(5)/Al$_2$O$_3$(95) | 152 | 81.4 | 98.4 | 1.6 |
| 8 | CaCl$_2$(5)/Al$_2$O$_3$(95) | 154 | 67.6 | 90.5 | 9.5 |
| 9 | SrCl$_2$(5)/Al$_2$O$_3$(95) | 155 | 70.8 | 97.0 | 3.0 |
| 10 | BaCl$_2$(5)/Al$_2$O$_3$(95) | 157 | 66.1 | 96.7 | 3.3 |
| 11 | YCl$_3$(5)/Al$_2$O$_3$(95) | 156 | 78.5 | 98.1 | 1.9 |
| 12 | ScCl$_3$(5)/Al$_2$O$_3$(95) | 154 | 71.5 | 97.7 | 2.3 |
| 13 | LaCl$_3$(5)/Al$_2$O$_3$(95) | 160 | 83.6 | 98.6 | 1.4 |
| 14 | TiCl$_3$(5)/Al$_2$O$_3$(95) | 151 | 57.5 | 95.4 | 4.6 |
| 15 | VCl$_3$(5)/Al$_2$O$_3$(95) | 152 | 46.0 | 96.4 | 3.6 |

TABLE 2

| Example | Catalyst (wt %) | Reaction Temperature (° C.) | Yield of Dichloropropanol (%) | Composition Ratio (mol %) | |
|---|---|---|---|---|---|
| | | | | 2,3-Dichloro-1-propanol | 1,3-Dichloro-2-propanol |
| 16 | CrCl$_2$(5)/Al$_2$O$_3$(95) | 155 | 68.0 | 97.0 | 3.0 |
| 17 | WCl$_6$(5)/Al$_2$O$_3$(95) | 147 | 40.1 | 94.7 | 5.3 |

TABLE 2-continued

| Example | Catalyst (wt %) | Reaction Temperature (° C.) | Yield of Dichloropropanol (%) | Composition Ratio (mol %) 2,3-Dichloro-1-propanol | Composition Ratio (mol %) 1,3-Dichloro-2-propanol |
|---|---|---|---|---|---|
| 18 | $MnCl_2(5)/Al_2O_3(95)$ | 153 | 70.3 | 97.3 | 2.7 |
| 19 | $ReCl_3(5)/Al_2O_3(95)$ | 155 | 68.0 | 95.4 | 4.6 |
| 20 | $FeCl_2(5)/Al_2O_3(95)$ | 158 | 71.9 | 90.8 | 9.2 |
| 21 | $FeCl_3(5)/Al_2O_3(95)$ | 159 | 70.9 | 90.5 | 9.5 |
| 22 | $RuCl_3(5)/Al_2O_3(95)$ | 159 | 72.0 | 92.2 | 7.8 |
| 23 | $CoCl_2(5)/Al_2O_3(95)$ | 160 | 68.0 | 98.0 | 2.0 |
| 24 | $RhCl_3(5)/Al_2O_3(95)$ | 158 | 72.1 | 93.2 | 6.8 |
| 25 | $NiCl_2(5)/Al_2O_3(95)$ | 160 | 65.0 | 93.8 | 6.2 |
| 26 | $PdCl_2(5)/Al_2O_3(95)$ | 161 | 31.2 | 66.8 | 33.2 |
| 27 | $H_2PtCl_4(5)/Al_2O_3(95)$ | 155 | 60.4 | 76.8 | 23.2 |
| 28 | $CuCl(5)/Al_2O_3(95)$ | 152 | 62.7 | 93.5 | 6.5 |
| 29 | $CuCl_2(5)/Al_2O_3(95)$ | 152 | 62.7 | 94.6 | 5.4 |
| 30 | $AgCl(5)/Al_2O_3(95)$ | 167 | 63.6 | 95.6 | 4.4 |

TABLE 3

| Example | Catalyst (wt %) | Reaction Temperature (° C.) | Yield of Dichloropropanol (%) | Composition Ratio (mol %) 2,3-Dichloro-1-propanol | Composition Ratio (mol %) 1,3-Dichloro-2-propanol |
|---|---|---|---|---|---|
| 31 | $ZnCl_2(5)/Al_2O_3(95)$ | 163 | 83.7 | 97.5 | 2.5 |
| 32 | $ZnF_2(5)/Al_2O_3(95)$ | 155 | 84.5 | 98.5 | 1.5 |
| 33 | $ZnBr_2(5)/Al_2O_3(95)$ | 152 | 82.0 | 98.4 | 1.6 |
| 34 | $ZnI_2(5)/Al_2O_3(95)$ | 152 | 79.6 | 98.2 | 1.8 |
| 35 | $ZnO(5)/Al_2O_3(95)$ | 163 | 82.4 | 98.3 | 1.7 |
| 36 | $ZnSO_4(5)/Al_2O_3(95)$ | 163 | 72.8 | 97.2 | 2.8 |
| 37 | $Zn_3(PO_4)_2(5)/Al_2O_3(95)$ | 153 | 74.8 | 98.0 | 2.0 |
| 38 | $Ga_2O_3(5)/Al_2O_3(95)$ | 159 | 47.2 | 96.8 | 3.2 |
| 39 | $InCl_3(5)/Al_2O_3(95)$ | 160 | 64.7 | 97.3 | 2.7 |
| 40 | $SnCl_2(5)/Al_2O_3(95)$ | 156 | 61.1 | 87.4 | 12.6 |
| 41 | $PbCl_2(5)/Al_2O_3(95)$ | 152 | 62.7 | 96.3 | 3.7 |
| 42 | $PbO(5)/Al_2O_3(95)$ | 155 | 67.1 | 97.1 | 2.9 |
| 43 | $Sb_2O_5(5)/Al_2O_3(95)$ | 158 | 74.2 | 97.5 | 2.5 |
| 44 | $BiCl_3(5)/Al_2O_3(95)$ | 158 | 70.2 | 97.2 | 2.8 |
| 45 | $Al_2O_3(100)$ | 152 | 66.0 | 96.4 | 3.6 |

TABLE 4

| Example | Catalyst (wt %) | Reaction Temperature (° C.) | Yield of Dichloropropanol (%) | Composition Ratio (mol %) 2,3-Dichloro-1-propanol | Composition Ratio (mol %) 1,3-Dichloro-2-propanol |
|---|---|---|---|---|---|
| 46 | $ZrO_2(100)$ | 155 | 68.0 | 97.0 | 3.0 |
| 47 | $Nb_2O_5(100)$ | 147 | 60.1 | 94.7 | 5.3 |
| 48 | $TiO_2(100)$ | 150 | 65.1 | 95.7 | 4.3 |
| 49 | $ZnCl_2(5)/Al_2O_3(95)$ | 131 | 88.5 | 98.9 | 1.1 |
| 50 | $ZnCl_2(5)/Al_2O_3(95)$ | 152 | 85.0 | 97.4 | 2.6 |
| 51 | $ZnCl_2(5)/Al_2O_3(95)$ | 168 | 78.8 | 98.2 | 1.8 |
| 52 | $ZnCl_2(5)/Al_2O_3(95)$ | 168 | 77.8 | 98.0 | 2.0 |
| 53 | $ZnCl_2(4.9) + LiCl(1.5)/Al_2O_3(93.6)$ molar ratio: Zn/Li = 1/1 | 155 | 80.8 | 98.3 | 1.7 |
| 54 | $ZnCl_2(4.9) + NaCl(2.1)/Al_2O_3(93.0)$ molar ratio: Zn/Na = 1/1 | 157 | 81.7 | 98.4 | 1.6 |
| 55 | $ZnCl_2(4.9) + KCl(2.7)/Al_2O_3(92.5)$ molar ratio: Zn/K = 1/1 | 154 | 77.4 | 98.1 | 1.9 |
| 56 | $ZnCl_2(4.8) + RbCl(4.3)/Al_2O_3(91.0)$ molar ratio: Zn/Rb = 1/1 | 152 | 72.1 | 97.7 | 2.3 |
| 57 | $ZnCl_2(4.7) + CsCl(5.8)/Al_2O_3(89.5)$ molar ratio: Zn/Cs = 1/1 | 152 | 75.8 | 98.0 | 2.0 |
| 58 | $ZnCl_2(4.9) + BeCl_2(2.9)/Al_2O_3(92.3)$ molar ratio: Zn/Be = 1/1 | 157 | 86.9 | 98.3 | 1.7 |

TABLE 4-continued

| Example | Catalyst (wt %) | Reaction Temperature (° C.) | Yield of Dichloropropanol (%) | Composition Ratio (mol %) 2,3-Dichloro-1-propanol | Composition Ratio (mol %) 1,3-Dichloro-2-propanol |
|---|---|---|---|---|---|
| 59 | ZnCl$_2$(4.8) + MgCl$_2$(3.4)/Al$_2$O$_3$(91.8) molar ratio: Zn/Mg = 1/1 | 160 | 96.8 | 99.6 | 0.4 |
| 60 | ZnCl$_2$(4.8) + CaCl$_2$(3.9)/Al$_2$O$_3$(91.3) molar ratio: Zn/Ca = 1/1 | 158 | 89.2 | 99.0 | 1.0 |

TABLE 5

| Example | Catalyst (wt %) | Reaction Temperature (° C.) | Yield of Dichloropropanol (%) | Composition Ratio (mol %) 2,3-Dichloro-1-propanol | Composition Ratio (mol %) 1,3-Dichloro-2-propanol |
|---|---|---|---|---|---|
| 61 | ZnCl$_2$(4.7) + SrCl$_2$(5.5)/Al$_2$O$_3$(89.8) molar ratio: Zn/Sr = 1/1 | 158 | 85.6 | 98.4 | 1.6 |
| 62 | ZnCl$_2$(4.7) + BaCl$_2$(7.1)/Al$_2$O$_3$(88.2) molar ratio: Zn/Ba = 1/1 | 160 | 82.1 | 98.0 | 2.0 |
| 63 | ZnCl$_2$(4.7) + YCl$_3$(6.7)/Al$_2$O$_3$(88.7) molar ratio: Zn/Y = 1/1 | 164 | 87.5 | 98.2 | 1.8 |
| 64 | ZnCl$_2$(4.7) + ScCl$_3$(5.3)/Al$_2$O$_3$(90.0) molar ratio: Zn/Sc = 1/1 | 155 | 85.5 | 98.3 | 1.7 |
| 65 | ZnCl$_2$(4.6) + LaCl$_3$(8.3)/Al$_2$O$_3$(87.2) molar ratio: Zn/La = 1/1 | 157 | 86.0 | 98.4 | 1.6 |
| 66 | ZnCl$_2$(4.7) + TiCl$_3$(5.4)/Al$_2$O$_3$(89.9) molar ratio: Zn/Ti = 1/1 | 155 | 76.0 | 95.4 | 4.6 |
| 67 | ZnCl$_2$(4.7) + VCl$_3$(5.5)/Al$_2$O$_3$(89.8) molar ratio: Zn/V = 1/1 | 158 | 74.8 | 94.4 | 5.6 |
| 68 | ZnCl$_2$(4.8) + CrCl$_2$(4.3)/Al$_2$O$_3$(90.9) molar ratio: Zn/Cr = 1/1 | 159 | 73.1 | 95.6 | 4.4 |
| 69 | ZnCl$_2$(4.4) + WCl$_6$(12.7)/Al$_2$O$_3$(82.9) molar ratio: Zn/W = 1/1 | 157 | 72.1 | 94.6 | 5.4 |
| 70 | ZnCl$_2$(4.8) + MnCl$_2$(4.4)/Al$_2$O$_3$(90.8) molar ratio: Zn/Mn = 1/1 | 161 | 89.9 | 98.5 | 1.5 |
| 71 | ZnCl$_2$(4.5) + ReCl$_3$(9.7)/Al$_2$O$_3$(85.8) molar ratio: Zn/Re = 1/1 | 158 | 78.1 | 95.8 | 4.2 |
| 72 | ZnCl$_2$(4.8) + FeCl$_2$(4.4)/Al$_2$O$_3$(90.8) molar ratio: Zn/Fe = 1/1 | 158 | 70.1 | 97.7 | 2.3 |
| 73 | ZnCl$_2$(4.7) + FeCl$_3$(5.6)/Al$_2$O$_3$(89.7) molar ratio: Zn/Fe = 1/1 | 158 | 73.1 | 95.4 | 4.6 |
| 74 | ZnCl$_2$(4.7) + RuCl$_3$(7.1)/Al$_2$O$_3$(88.3) molar ratio: Zn/Ru = 1/1 | 158 | 70.1 | 94.5 | 5.5 |
| 75 | ZnCl$_2$(4.8) + CoCl$_2$(4.5)/Al$_2$O$_3$(90.7) molar ratio: Zn/Co = 1/1 | 163 | 88.1 | 98.4 | 1.6 |

TABLE 6

| Example | Catalyst (wt %) | Reaction Temperature (° C.) | Yield of Dichloropropanol (%) | Composition Ratio (mol %) 2,3-Dichloro-1-propanol | Composition Ratio (mol %) 1,3-Dichloro-2-propanol |
|---|---|---|---|---|---|
| 76 | ZnCl$_2$(4.6) + RhCl$_3$(7.1)/Al$_2$O$_3$(88.2) molar ratio: Zn/Rh = 1/1 | 163 | 80.1 | 96.4 | 3.6 |
| 77 | ZnCl$_2$(4.8) + NiCl$_2$(4.8)/Al$_2$O$_3$(90.5) molar ratio: Zn/Ni = 1/1 | 164 | 82.2 | 98.1 | 1.9 |
| 78 | ZnCl$_2$(4.7) + PdCl$_2$(6.1)/Al$_2$O$_3$(89.2) molar ratio: Zn/Pd = 1/1 | 163 | 78.1 | 92.3 | 7.7 |
| 79 | ZnCl$_2$(4.5) + H$_2$PtCl$_4$(11.1)/Al$_2$O$_3$(84.5) molar ratio: Zn/Pt = 1/1 | 163 | 76.1 | 93.7 | 6.7 |
| 80 | ZnCl$_2$(4.8) + CuCl(3.5)/Al$_2$O$_3$(91.7) molar ratio: Zn/Cu = 1/1 | 163 | 80.1 | 98.0 | 2.0 |
| 81 | ZnCl$_2$(4.8) + CuCl$_2$(4.7)/Al$_2$O$_3$(90.5) molar ratio: Zn/Cu = 1/1 | 164 | 78.1 | 97.9 | 2.1 |
| 82 | ZnCl$_2$(4.8) + AgCl(5.0)/Al$_2$O$_3$(90.3) molar ratio: Zn/Ag = 1/1 | 163 | 78.1 | 95.1 | 4.9 |
| 83 | ZnCl$_2$(4.6) + InCl$_3$(7.5)/Al$_2$O$_3$(87.9) molar ratio: Zn/In = 1/1 | 154 | 72.8 | 98.0 | 2.0 |

TABLE 6-continued

| Example | Catalyst (wt %) | Reaction Temperature (° C.) | Yield of Dichloropropanol (%) | Composition Ratio (mol %) 2,3-Dichloro-1-propanol | Composition Ratio (mol %) 1,3-Dichloro-2-propanol |
|---|---|---|---|---|---|
| 84 | $ZnCl_2$(4.7) + $SnCl_2$(6.5)/$Al_2O_3$(88.8) molar ratio: Zn/Sn = 1/1 | 157 | 77.5 | 98.3 | 1.7 |
| 85 | $ZnCl_2$(4.5) + $PbCl_2$(9.3)/$Al_2O_3$(86.2) molar ratio: Zn/Pb = 1/1 | 155 | 77.5 | 97.3 | 2.7 |
| 86 | $ZnCl_2$(4.7) + $Sb_2O_5$(5.6)/$Al_2O_3$(89.7) molar ratio: Zn/Sb = 1/1 | 156 | 80.5 | 98.7 | 1.3 |
| 87 | $ZnCl_2$(4.5) + $BiCl_3$(10.4)/$Al_2O_3$(85.2) molar ratio: Zn/Bi = 1/1 | 154 | 77.2 | 98.2 | 1.8 |
| 88 | $MgCl_2$(4.7) + $CaCl_2$(5.5)/$Al_2O_3$(89.8) molar ratio: Mg/Ca = 1/1 | 155 | 89.2 | 98.9 | 1.1 |
| 89 | $InCl_3$(4.8) + $BaCl_2$(4.5)/$Al_2O_3$(90.7) molar ratio: In/Ba = 1/1 | 162 | 88.4 | 98.2 | 1.8 |
| 90 | $ZnCl_2$(4.8) + $MgCl_2$(3.4)/$ZrO_2$(91.8) molar ratio: Zn/Mg = 1/1 | 166 | 94.8 | 99.6 | 0.4 |

TABLE 7

| Example | Catalyst (wt %) | Reaction Temperature (° C.) | Yield of Dichloropropanol (%) | Composition Ratio (mol %) 2,3-Dichloro-1-propanol | Composition Ratio (mol %) 1,3-Dichloro-2-propanol |
|---|---|---|---|---|---|
| 91 | $ZnCl_2$(4.8) + $MgCl_2$(3.4)/$TiO_2$(91.8) molar ratio: Zn/Mg = 1/1 | 165 | 94.3 | 99.3 | 0.7 |
| 92 | $ZnCl_2$(4.8) + $MgCl_2$(3.4)/$SiO_2$(91.8) molar ratio: Zn/Mg = 1/1 | 167 | 94.0 | 99.1 | 0.9 |
| 93 | $ZnCl_2$(4.8) + $MgCl_2$(3.4)/SiC(91.8) molar ratio: Zn/Mg = 1/1 | 166 | 95.8 | 99.5 | 0.5 |
| 94 | $ZnCl_2$(4.8) + $MgCl_2$(3.4)/$Al_2O_3$(91.8) molar ratio: Zn/Mg = 1/1 | 170 | 88.8 | 99.1 | 0.9 |
| 95 | $ZnCl_2$(4.8) + $MgCl_2$(3.4)/$Al_2O_3$(91.8) molar ratio: Zn/Mg = 1/1 | 171 | 91.8 | 99.6 | 0.4 |
| 96 | $ZnCl_2$(4.8) + $MgCl_2$(3.4)/$Al_2O_3$(91.8) molar ratio: Zn/Mg = 1/1 | 155 | 93.8 | 99.6 | 0.4 |
| 97 | $ZnCl_2$(4.8) + $MgCl_2$(3.4)/$Al_2O_3$(91.8) molar ratio: Zn/Mg = 1/1 | 151 | 95.1 | 99.6 | 0.4 |
| 98 | $ZnCl_2$(4.8) + $MgCl_2$(3.4)/$Al_2O_3$(91.8) molar ratio: Zn/Mg = 1/1 | 160 | 96.1 | 99.7 | 0.3 |
| 99 | $ZnCl_2$(4.8) + $MgCl_2$(3.4)/$Al_2O_3$(91.8) molar ratio: Zn/Mg = 1/1 | 158 | 96.4 | 99.6 | 0.4 |
| 100 | none | 142 | 10.4 | 99.2 | 0.8 |
| 101 | $TeCl_4$(5)/$Al_2O_3$(95) | 152 | 73.2 | 95.3 | 4.7 |
| 102 | $ZnCl_2$(4.6) + $TeCl_4$(9.0)/$Al_2O_3$(86.5) molar ratio: Zn/Te = 1/1 | 157 | 87.7 | 95.9 | 4.1 |
| 103 | $ZnCl_2$(4.8) + $MgCl_2$(3.4)/$Al_2O_3$(91.8) molar ratio: Zn/Mg = 1/1 | 159 | 98.1 | 99.7 | 0.3 |
| 104 | activated carbon (100) | 151 | 58.2 | 95.0 | 5.0 |

TABLE 8

| Example | Catalyst (wt %) | Reaction Temperature (° C.) | Yield of Dichloropropanol (%) | Composition Ratio (mol %) 2,3-Dichloro-1-propanol | Composition Ratio (mol %) 1,3-Dichloro-2-propanol |
|---|---|---|---|---|---|
| 105 | $ZnCl_2$(4.8) + $MgCl_2$(3.3) + NaCl(1.0)/$Al_2O_3$(90.9) molar ratio: Zn/Mg/Na = 1/1/0.5 | 162 | 96.9 | 99.7 | 0.3 |
| 106 | $ZnCl_2$(4.7) + $MgCl_2$(3.3) + $CaCl_2$(1.9)/$Al_2O_3$(90.0) molar ratio: Zn/Mg/Ca = 1/1/0.5 | 163 | 97.1 | 99.8 | 0.2 |
| 107 | $ZnCl_2$(4.7) + $MgCl_2$(3.3) + $SrCl_2$(2.7)/$Al_2O_3$(89.3) molar ratio: Zn/Mg/Sr = 1/1/0.5 | 161 | 97.0 | 99.6 | 0.4 |
| 108 | $ZnCl_2$(4.7) + $MgCl_2$(3.3) + $YCl_3$(3.3)/$Al_2O_3$(88.7) molar ratio: Zn/Mg/Y = 1/1/0.5 | 163 | 96.9 | 99.7 | 0.3 |

TABLE 8-continued

| Example | Catalyst (wt %) | Reaction Temperature (° C.) | Yield of Dichloropropanol (%) | Composition Ratio (mol %) 2,3-Dichloro-1-propanol | 1,3-Dichloro-2-propanol |
|---|---|---|---|---|---|
| 109 | $ZnCl_2(4.7)$ + $MgCl_2(3.3)$ + $MnCl_2(2.2)$/ $Al_2O_3(89.8)$ molar ratio: Zn/Mg/Mn = 1/1/0.5 | 162 | 97.1 | 99.6 | 0.4 |
| 110 | $ZnCl_2(4.7)$ + $MgCl_2(3.3)$ + $CoCl_2(2.3)$/ $Al_2O_3(89.7)$ molar ratio: Zn/Mg/Co = 1/1/0.5 | 164 | 96.9 | 99.6 | 0.4 |
| 111 | $ZnCl_2(4.6)$ + $MgCl_2(3.2)$ + $BiCl_3(5.3)$/ $Al_2O_3(86.9)$ molar ratio: Zn/Mg/Bi = 1/1/0.5 | 165 | 97.0 | 99.6 | 0.4 |
| 112 | $ZnCl_2(4.6)$ + $MgCl_2(3.2)$ + $TeCl_4(4.6)$/ $Al_2O_3(87.6)$ molar ratio: Zn/Mg/Te = 1/1/0.5 | 163 | 97.1 | 99.6 | 0.4 |

According to the present invention, dichloropropanol can be obtained in a high yield and at a high selectivity. Also, dichloropropanol can be produced without the problems encountered in a conventional liquid phase reaction, such as need of a step for the separation and recovery of hydrochloric acid, loss of hydrochloric acid in the recovery step and energy loss accompanying the cooling.

Furthermore, according to the present invention, epichlorohydrin can be efficiently manufactured from dichloropropanol obtained by reacting allyl alcohol with chlorine in a gaseous phase.

What is claimed is:

1. A process for producing dichloropropanol, comprising reacting allyl alcohol with chlorine in a gaseous phase.

2. A process according to claim 1, wherein the reaction is performed in the presence of a catalyst.

3. A process according to claim 2, wherein the catalyst contains at least one element selected from elements of Groups 1 to 16 of the long-form Periodic Table or at least one compound containing the at least one element.

4. A process according to claim 3, wherein the compound containing the at least one element selected from elements of Groups 1 to 16 of the long-form Periodic Table is a halide or an oxide.

5. A process according to claim 2, wherein the catalyst is a supported catalyst.

6. A process according to claim 2, wherein the process comprises blending and diluting the catalyst with another filler.

7. A process according to claim 1 or 2, wherein the process comprises performing the reacting in the presence of water.

8. A process according to claim 1 or 2, wherein the process comprises adding a diluent.

9. A process according to claim 1 or 2, wherein the reaction temperature is from 70 to 300° C.

10. A process according to claim 1 or 2, wherein the reaction pressure is from 10 to 1,000 kPa.

11. A process according to claim 1 or 2, wherein the molar ratio of chlorine to allyl alcohol is from 0.001 to 1.5.

12. A process for producing epichlorohydrin comprising:

a first step of reacting allyl alcohol with chlorine in a gaseous phase to produce dichloropropanol; and a second step of dehydrochlorinating dichloropropanol obtained at the first step to produce epichlorohydrin.

13. A process according to claim 12, wherein the process comprises performing the first step reaction in the presence of a catalyst.

14. A process according to claim 13, wherein the catalyst contains at least one element selected from elements of Groups 1 to 16 of the long-form Periodic Table or at least one compound containing the at least one element.

15. A process according to claim 14, wherein the compound containing the at least one element selected from elements of Groups 1 to 16 of the long-form Periodic Table is a halide or an oxide.

16. A process according to claim 13, wherein the catalyst is a supported catalyst.

17. A process according to claim 13, wherein the process comprises blending and diluting the catalyst with another filler.

18. A process according to claim 12 or 13, wherein the process comprises performing the first step in the presence of water.

19. A process according to claim 12 or 13, wherein the process comprises adding a diluent at the first step.

20. A process according to claim 12 or 13, wherein the reaction temperature at the first step is from 70 to 300° C.

21. A process according to claim 12 or 13, wherein the reaction pressure at the first step is from 10 to 1,000 kPa.

22. A process according to claim 12 or 13, wherein the molar ratio of chlorine to allyl alcohol at the first step is from 0.001 to 1.5.

* * * * *